US012765857B2

(12) United States Patent
Kawamura

(10) Patent No.: US 12,765,857 B2
(45) Date of Patent: Oct. 20, 2026

(54) X-RAY IMAGING APPARATUS, PROCESSING APPARATUS, AND EXAMINATION METHOD

(71) Applicant: SHIMADZU CORPORATION, Kyoto (JP)

(72) Inventor: Takahiro Kawamura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 91 days.

(21) Appl. No.: 19/031,444

(22) Filed: Jan. 18, 2025

(65) Prior Publication Data

US 2025/0261920 A1 Aug. 21, 2025

(30) Foreign Application Priority Data

Feb. 21, 2024 (JP) ................................ 2024-024773

(51) Int. Cl.
*A61B 6/00* (2024.01)
*A61B 6/46* (2024.01)

(52) U.S. Cl.
CPC ............ *A61B 6/5294* (2013.01); *A61B 6/461* (2013.01); *A61B 6/468* (2013.01); *A61B 6/54* (2013.01)

(58) Field of Classification Search
CPC ....... A61B 6/461; A61B 6/468; A61B 6/5294; A61B 6/54
See application file for complete search history.

(56) References Cited

U.S. PATENT DOCUMENTS 5,008,942 A * 4/1991 Kikuchi .................. A61B 6/00 704/270
5,533,082 A * 7/1996 Gronemeyer .......... A61B 6/035 378/65
5,807,256 A * 9/1998 Taguchi .................... G06T 7/11 600/300

(Continued)

OTHER PUBLICATIONS

Kumar, S et al., "A novel multimodal fusion framework for early diagnosis and accurate classification of COVID-19 patients using X-ray images and speech signal processing techniques", 2022, Computer Methods and Programs in Biomedicine, 226, 107109, 1-13 (Year: 2022).*

(Continued)

*Primary Examiner* — Blake C Riddick
(74) *Attorney, Agent, or Firm* — Muir Patent Law, PLLC

(57) ABSTRACT

An X-ray imaging apparatus according to this invention includes an X-ray-image-and-voice-information collector for collecting a plurality of X-ray images based on detection results of X-rays with which a patient is irradiated, and for collecting voice information on the patient's voice input from a voice information input part; an X-ray image preserver for preserving the plurality of X-ray images collected together with time information; a voice information preserver for preserving the voice information collected together with time information; a timing identifier for identifying a timing in which the speech of the patient is different from the examination sentence based on the voice information preserved; an X-ray image identifier for identifying a corresponding X-ray image that corresponds to the timing in the plurality of X-ray images preserved; and a display controller for directing a display to display the corresponding X-ray image.

9 Claims, 3 Drawing Sheets

(56) References Cited

U.S. PATENT DOCUMENTS

| | | | | |
|---|---|---|---|---|
| 6,047,257 | A * | 4/2000 | Dewaele | A61B 6/4494<br>704/E15.044 |
| 6,379,043 | B1 * | 4/2002 | Zylka | A61B 6/547<br>378/207 |
| 2003/0026464 | A1 * | 2/2003 | Kamiyama | G16Z 99/00<br>382/128 |
| 2003/0033151 | A1 * | 2/2003 | Vozick | A61B 5/7475<br>704/E15.045 |
| 2003/0068011 | A1 * | 4/2003 | Johnson | A61B 5/7475<br>378/115 |
| 2003/0160682 | A1 * | 8/2003 | Yamada | G16H 40/20<br>340/531 |
| 2005/0027197 | A1 * | 2/2005 | Segawa | A61B 6/00<br>600/463 |
| 2005/0065412 | A1 * | 3/2005 | Shiomi | A61B 5/4863<br>600/300 |
| 2005/0203386 | A1 * | 9/2005 | Heigl | A61B 6/583<br>600/427 |
| 2008/0056447 | A1 * | 3/2008 | Boese | A61B 6/504<br>382/128 |
| 2008/0255849 | A9 * | 10/2008 | Gustafson | A61B 6/468<br>704/E15.045 |
| 2008/0267346 | A1 * | 10/2008 | Poorter | A61B 6/542<br>378/16 |
| 2009/0054755 | A1 * | 2/2009 | Shiibashi | G16H 15/00<br>600/407 |
| 2009/0097615 | A1 * | 4/2009 | Fischer | G06T 5/50<br>378/98.3 |
| 2009/0225935 | A1 * | 9/2009 | Eliasson | A61B 6/502<br>378/37 |
| 2010/0329534 | A1 * | 12/2010 | Biermann | A61B 6/027<br>378/197 |
| 2011/0288853 | A1 * | 11/2011 | Butzine | A61B 6/4405<br>704/8 |
| 2013/0208851 | A1 * | 8/2013 | Kimoto | A61B 6/461<br>378/8 |
| 2015/0063545 | A1 * | 3/2015 | Lee | A61B 6/545<br>378/91 |
| 2016/0166222 | A1 * | 6/2016 | Kim | A61B 6/0414<br>378/37 |
| 2016/0192894 | A1 * | 7/2016 | Ohishi | A61B 6/463<br>715/771 |
| 2016/0213344 | A1 * | 7/2016 | Yi | A61B 6/4241 |
| 2017/0071573 | A1 * | 3/2017 | Takahashi | A61B 6/462 |
| 2017/0300470 | A1 * | 10/2017 | Khamis | G06F 40/242 |
| 2018/0303667 | A1 * | 10/2018 | Peyman | A61B 5/0095 |
| 2019/0139642 | A1 * | 5/2019 | Roberge | G06F 3/013 |
| 2019/0189122 | A1 * | 6/2019 | Yokoyama | G10L 15/24 |
| 2020/0066405 | A1 * | 2/2020 | Peyman | G06N 3/08 |
| 2020/0162839 | A1 * | 5/2020 | Whitten | H04L 67/51 |
| 2020/0383655 | A1 * | 12/2020 | Fujii | A61B 6/46 |
| 2021/0133969 | A1 * | 5/2021 | Sasaki | A61B 5/0077 |
| 2021/0212648 | A1 * | 7/2021 | Bailey, Sr. | A61B 6/508 |
| 2021/0378613 | A1 * | 12/2021 | Okuno | A61B 6/46 |
| 2021/0393231 | A1 * | 12/2021 | Nishijima | A61B 6/461 |
| 2022/0061787 | A1 * | 3/2022 | Schulze-Ganzlin | A61B 6/512 |
| 2022/0096029 | A1 * | 3/2022 | Ariyama | A61B 6/032 |
| 2022/0139528 | A1 * | 5/2022 | Nishitaka | G16H 30/20<br>382/103 |
| 2022/0240779 | A1 * | 8/2022 | Peyman | A61B 5/0022 |
| 2022/0327698 | A1 * | 10/2022 | Okumura | G06T 7/0012 |
| 2022/0386971 | A1 * | 12/2022 | Na | A61B 6/0407 |
| 2023/0169649 | A1 * | 6/2023 | Rao | A61B 6/4452<br>378/62 |
| 2023/0293134 | A1 * | 9/2023 | Horiuchi | A61B 6/548<br>378/62 |
| 2024/0099669 | A1 * | 3/2024 | Gatayama | A61B 6/54 |
| 2024/0177837 | A1 * | 5/2024 | Arima | G16H 30/20 |
| 2024/0266041 | A1 * | 8/2024 | Nishioka | A61B 6/461 |
| 2024/0321444 | A1 * | 9/2024 | Hayashi | A61B 6/467 |
| 2024/0358223 | A1 * | 10/2024 | Kimura | A61B 1/000094 |
| 2024/0382102 | A1 * | 11/2024 | Nakayama | G01R 33/283 |
| 2025/0099055 | A1 * | 3/2025 | Horiuchi | A61B 6/50 |
| 2025/0104846 | A1 * | 3/2025 | Horiuchi | G10L 25/57 |
| 2025/0147525 | A1 * | 5/2025 | Goto | A61B 6/0407 |
| 2025/0149157 | A1 * | 5/2025 | Goto | G16H 30/20 |
| 2025/0241611 | A1 * | 7/2025 | Tsuchida | A61B 6/547 |

OTHER PUBLICATIONS

Hajime Watanabe et al., "Videofluorographic Analysis of Articulation Movements and of Velopharyngeal Closure during Phonation in Cleft Lip and Palate Children with Two-stage Palatoplasty," Journal of Japanese Cleft Palate Association 22, 108-123, 1997.

* cited by examiner

X-RAY IMAGING APPARATUS, PROCESSING APPARATUS, AND EXAMINATION METHOD

CROSS-REFERENCE TO RELATED APPLICATIONS

The related application number JP2024-024773, X-ray imaging apparatus, processing apparatus and examination method, Feb. 21, 2024, KAWAMURA Takahiro, upon which this patent application is based are hereby incorporated by reference.

BACKGROUND OF THE INVENTION

Field of the Invention

The present invention relates to an X-ray imaging apparatus, a processing apparatus and an examination method.

Description of the Background Art

Examination of speech of patients is known in the art. Such examination is disclosed, for example, in "Analysis of Movements of Articulatory Organs of Child Patients Who Had Two-Stage Palate Repair Using X-ray Television System", WATANABE Hajime and two others, Journal of Japanese Cleft Palate Association, Jul. 31, 1997, Volume 22, Issue 3, pages 108-123 (hereinafter "Non-Patent Document 1").

The above non-patent document 1 discloses that speech of patients is examined in examination of patients' articulation impairment (speech study). The articulation impairment refers to impairment of speech caused by patients' organs relating to speech (e.g., tongue, soft palate, and pharynx) or movements of the organs. In the speech study, speech of patients is recorded while X-ray images are captured by an X-ray imaging apparatus by using a contrast agent in the patients' organs relating to speech. Radiologists examine speech ability of the patients by observing the recorded speech of the patients and the X-ray images captured by X-ray imaging.

In such speech study stated in the above non-patent document 1, a relatively large number of X-ray images are acquired. For example, an imaging rate of X-ray imaging for examination of articulation impairment is 30 fps in a case of high imaging rate, and 300 to 400 X-ray images will be acquired in a single examination. Accordingly, the radiologists are required to find the X-ray images that are necessarily confirmed from such a large number of X-ray images in the examination of articulation impairment. In addition, if X-ray imaging is performed two or more times in the examination, time required to find the X-ray images that are necessarily confirmed increases with the number of imaging times. Also, a similar problem arises in a case in which speech of patients who have impairment other than articulation impairment is examined. For these reasons, it is desired to reduce burdens on the radiologists in examination of speech of patients.

SUMMARY OF THE INVENTION

The present invention is intended to solve the above problem, and one object of the present invention is to provide an X-ray imaging apparatus, a processing apparatus and an examination method capable of reducing burdens on radiologists in examination of speech of patients.

In order to attain the aforementioned object, an X-ray imaging apparatus according to a first aspect of the present invention includes an X-ray irradiator for irradiating a patient with X-rays; an X-ray detector for detecting the X-rays with which the patient is irradiated by the X-ray irradiator; an X-ray-image-and-voice-information collector for collecting a plurality of X-ray images based on detection results of the X-rays with which the patient is irradiated in a time width in which the patient produces speech of an examination sentence, and for collecting voice information on the patient's voice input from a voice information input part in a time width that at least partially overlaps the time width of the collection of the plurality of X-ray images; an X-ray image preserver for preserving the plurality of X-ray images, which are collected by the X-ray-image-and-voice-information collector, together with time information; a voice information preserver for preserving the voice information, which is collected by the X-ray-image-and-voice-information collector, together with time information; a timing identifier for identifying a timing in which the speech of the patient is different from the examination sentence based on the voice information preserved in the voice information preserver; an X-ray image identifier for identifying a corresponding X-ray image that corresponds to the timing in the plurality of X-ray images preserved in the X-ray image preserver; and a display controller for directing a display to display the corresponding X-ray image.

In order to attain the aforementioned object, an image processing apparatus according to a second aspect of the present invention includes an X-ray-image-and-voice-information collector for collecting a plurality of X-ray images based on detection results of the X-rays with which a patient is irradiated in a time width in which the patient produces speech of an examination sentence, and for collecting voice information on the patient's voice input from a voice information input part in a time width that at least partially overlaps the time width of the collection of the plurality of X-ray images; an X-ray image preserver for preserving the plurality of X-ray images, which are collected by the X-ray-image-and-voice-information collector, together with time information; a voice information preserver for preserving the voice information, which is collected by the X-ray-image-and-voice-information collector, together with time information; a timing identifier for identifying a timing in which the speech of the patient is different from the examination sentence based on the voice information preserved in the voice information preserver; an X-ray image identifier for identifying a corresponding X-ray image that corresponds to the timing in the plurality of X-ray images preserved in the X-ray image preserver; and a display controller for directing a display to display the corresponding X-ray image.

In order to attain the aforementioned object, an examination method according to a third aspect of the present invention includes a step of collecting a plurality of X-ray images based on detection results of the X-rays with which the patient is irradiated in a time width in which a patient produces speech of an examination sentence, and for collecting voice information on the patient's voice input from a voice information input part in a time width that at least partially overlaps the time width of the collection of the plurality of X-ray images; a step of preserving the plurality of X-ray images collected together with time information; a step of preserving the voice information collected together with time information; a step of identifying a timing in which speech of the patient is different from the examination sentence based on the voice information preserved; a step of identifying a corresponding X-ray image that corresponds to the timing in the plurality of X-ray images preserved; and a step of directing a display to display the corresponding X-ray image.

In the aforementioned X-ray imaging apparatus according to the first aspect, the aforementioned processing apparatus according to the second aspect and the aforementioned examination method according to the third aspect, as described above, a plurality of X-ray images are collected based on detection results of the X-rays with which the patient is irradiated in a time width in which a patient produces speech of an examination sentence, and for collecting voice information on the patient's voice input from a voice information input part in a time width that at least partially overlaps the time width of the collection of the plurality of X-ray images; the plurality of X-ray images collected are preserved together with time information; the voice information collected is preserved together with time information; a timing in which speech of the patient is different from the examination sentence is identified based on the voice information preserved; a corresponding X-ray image that corresponds to the timing is identified from the plurality of X-ray images preserved; and the corresponding X-ray image is displayed on a display. According to this configuration, it is possible to automatically identify and display the corresponding X-ray image, which is the X-ray image to be necessarily confirmed, in examination of speech of patients. Consequently, radiologists are not required to find the X-ray image to be necessarily confirmed from a large number of X-ray images by themselves. As a result, it is possible to reduce burdens on the radiologists in examination of speech of patients.

The foregoing and other objects, features, aspects and advantages of the present invention will become more apparent from the following detailed description of the present invention when taken in conjunction with the accompanying drawings.

DESCRIPTION OF THE PREFERRED EMBODIMENT

Embodiments embodying the present invention will be described with reference to the drawings.

Entire Configuration of X-Ray Imaging Apparatus

A configuration of an X-ray imaging apparatus 100 according to one embodiment of the present invention is now described with reference to FIG. 1.

Figure 1:
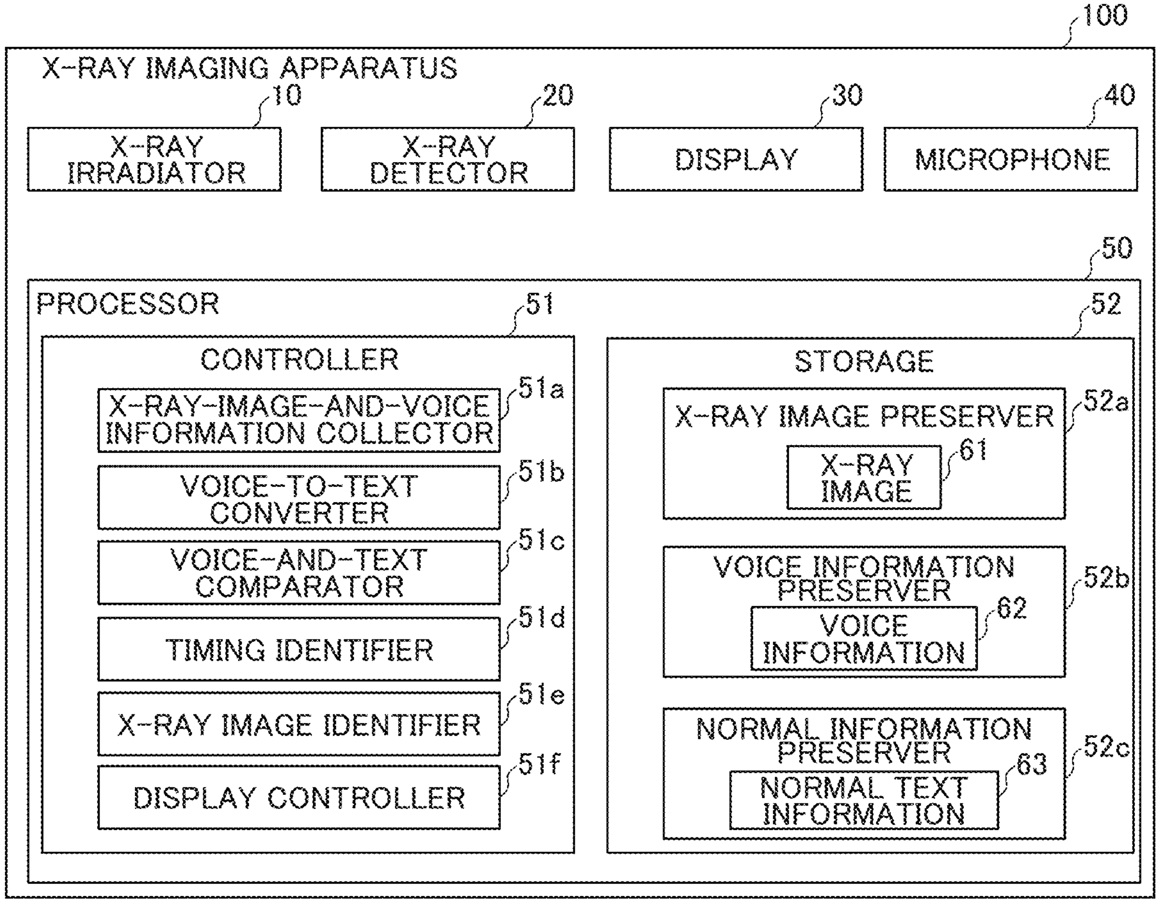
FIG. 1 is a block diagram showing an X-ray imaging apparatus according to one embodiment.

As shown in FIG. 1, the X-ray imaging apparatus 100 is an apparatus for capturing X-ray images of a patient by using X-rays. The X-ray imaging apparatus 100 is configured to acquire the X-ray images of the patient by fluoroscopic imaging or serial imaging (imaging using X-rays having intensity higher than fluoroscopic imaging). In this embodiment, the X-ray images of organs relating to the speech of the patient to examine the speech of the patient are acquired by capturing the X-ray images of the organs relating to speech of the patient (e.g., tongue, soft palate, and pharynx) by using the X-ray imaging apparatus 100. The X-ray imaging apparatus 100 is used for examination of patients' articulation impairment (speech study).

The X-ray imaging apparatus 100 includes an X-ray irradiator 10, an X-ray detector 20, a display 30, a microphone 40, and a processing part 50. The microphone 40 and the processing part 50 are examples of a "voice information input part" and a "processing apparatus," respectively, in the claims.

The X-ray irradiator 10 irradiates the patient with X-rays. The X-ray irradiator 10 includes an X-ray tube for generating the X-rays, and a collimator for adjusting an irradiation direction and an area of the X-rays generated by the X-ray tube.

The X-ray detector 20 detects the X-rays with which the patient is irradiated by the X-ray irradiator 10. The X-ray detector 20 includes an FPD (Flat Panel Detector) or an I. I. (Image Intensifier). The X-ray detector 20 is arranged to face the X-ray irradiator 10 to interpose the patient between them.

The X-ray images of the patient are captured by irradiating the patient with the X-rays from the X-ray irradiator 10 and by detecting the X-rays by using the X-ray detector 20. In the examination of the speech of the patient, the X-ray irradiator 10 and the X-ray detector 20 are arranged to face each other to interpose the organs relating to the speech of the patient between them. The X-ray detector 20 detects the X-rays when the organs relating to the speech of the patient are irradiated with the X-rays from the X-ray irradiator 10.

The display 30 includes a monitor, and displays information relating to X-ray imaging. The microphone 40 accepts input of voice information on the patient's voice. The microphone 40 is arranged at a position that allows the microphone to accept the input of voice information on the patient's voice in the examination of the speech of the patient.

The processing part 50 is a computer including a controller 51 and a storage 52. The controller 51 includes a processor such as a CPU (Central Processing Unit) and GPU (Graphics Processing Unit), and controls operation of parts of the X-ray imaging apparatus 100. The controller 51 as hardware includes an X-ray-image-and-voice-information collector 51*a*, a voice-to-text converter 51*b*, a voice-and-text comparator 51*c*, a timing identifier 51*d*, an X-ray image identifier 51*e*, and a display controller 51*f*, which are software functional blocks. The controller 51 serves as the X-ray-image-and-voice-information collector 51*a*, the voice-to-text converter 51*b*, the voice-and-text comparator 51*c*, the timing identifier 51*d*, the X-ray image identifier 51*e*, and the display controller 51*f* by executing a predetermined program.

The storage 52 includes a volatile storage device such as RAM (Random Access Memory), and a non-volatile storage device such as ROM (Read Only Memory), hard disk drive, solid state drive or the like, and stores information relating to the X-ray imaging. The storage 52 includes an X-ray image preserver 52*a*, a voice information preserver 52*b*, and a normal information preserver 52*c* as storage areas in the storage 52.

Configurations Relating to Patient's Speech Examination

Configurations of the X-ray imaging apparatus 100 relating to the examination of the speech of the patient are now described with reference to FIGS. 2 and 3.

In the examination of the speech of the patient, the patient produces speech of a predetermined examination sentence. The X-ray irradiator 10 irradiates the organs relating to the speech of the patient with X-rays, and the X-ray detector 20 detects the X-rays with which the organs relating to the speech of the patient are irradiated. The controller 51 acquires detection results of the X-rays with which the patient is irradiated from the X-ray detector 20, and generates X-ray images 61 based on the detection results acquired. A plurality of X-ray images 61 are generated at a predetermined frame rate. Also, the microphone 40 receives voice information 62 on voice of the patient who produces the speech of the examination sentence.

Figure 2:
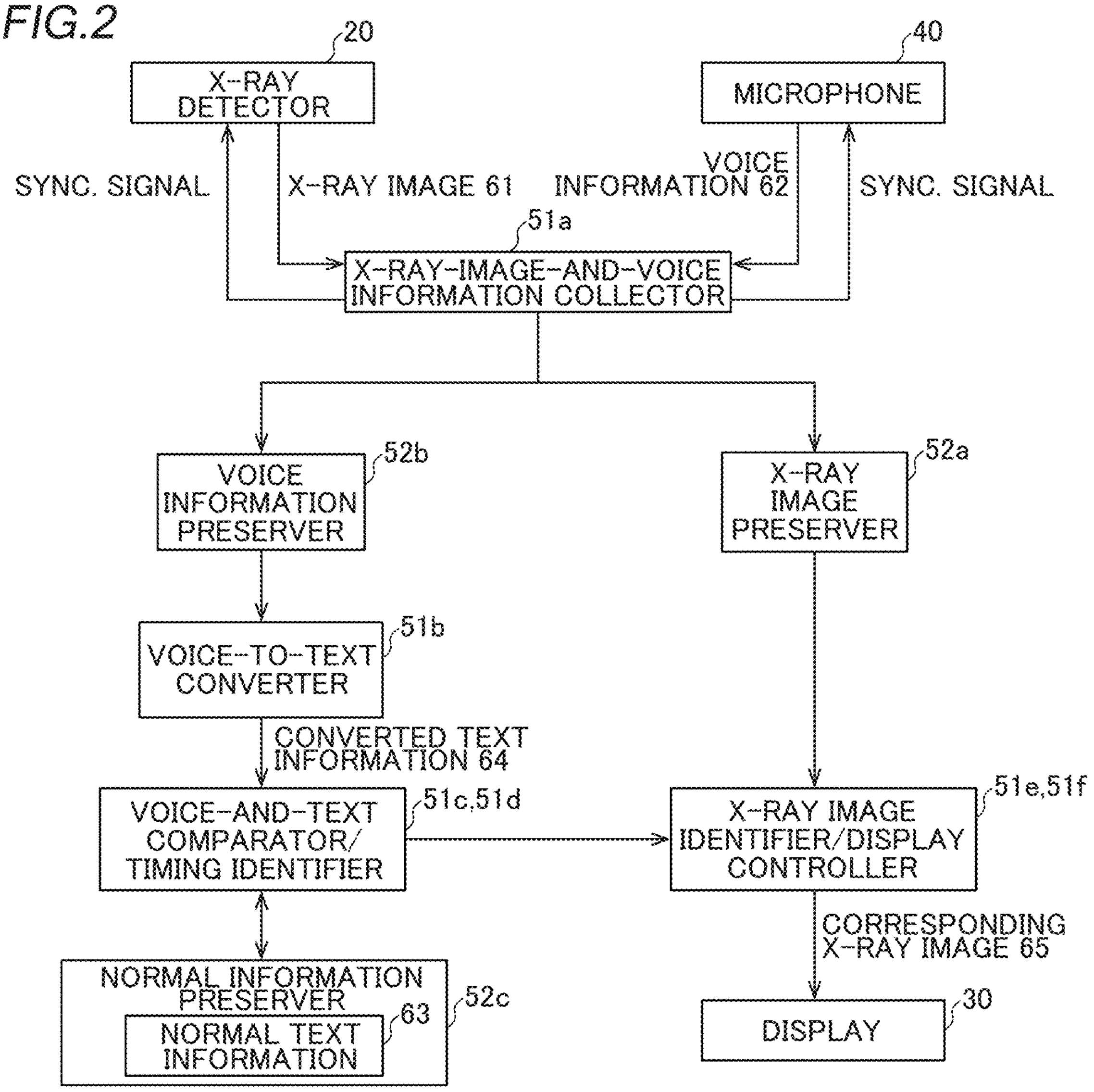
FIG. 2 is a schematic view illustrating control relating to examination of speech of a patient according to the one embodiment.
Figure 3:
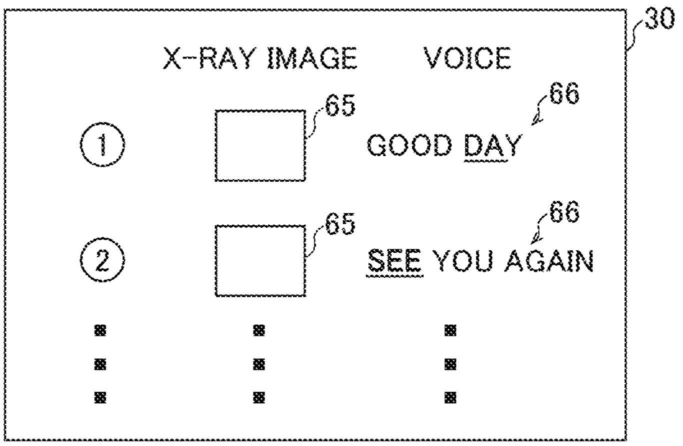
FIG. 3 is a schematic view illustrating images displayed on a display according to the one embodiment.

As shown in FIG. 2, the X-ray-image-and-voice-information collector 51*a* collects the plurality of X-ray images 61 based on the detection results of the X-rays with which the patient is irradiated in a time width in which the patient produces the speech of the examination sentence, and collects the voice information 62 on the patient's voice input from the microphone 40 in a time width that at least partially overlaps the time width of the collection of the plurality of X-ray images 61. Specifically, the X-ray-image-and-voice-information collector 51*a* collects the plurality of X-ray images 61 and the voice information 62 on the patient's voice in synchronization with each other. More specifically, the X-ray-image-and-voice-information collector 51*a* starts to collect both the plurality of X-ray images 61 and the voice information 62 in synchronization with the timing of start of irradiation of the organs relating to the speech of the patient with X-ray by the X-ray irradiator 10. Also, the X-ray-image-and-voice-information collector 51*a* terminates the collection of both the plurality of X-ray images 61 and the voice information 62 in synchronization with the timing of termination of the irradiation of the organs relating to the speech of the patient with X-ray by the X-ray irradiator 10.

The plurality of X-ray images 61 collected by the X-ray-image-and-voice-information collector 51*a* are preserved in the X-ray image preserver 52*a*. The X-ray image preserver 52*a* preserves the plurality of X-ray images 61, which are collected by the X-ray-image-and-voice-information collector 51*a*, together with time information (time logs). For example, the X-ray image preserver 52*a* preserves the plurality of X-ray images 61, which are collected by the X-ray-image-and-voice-information collector 51*a*, associated with elapsed time periods from the timing of the start of X-ray irradiation.

Also, the voice information 62, which is collected by the X-ray-image-and-voice-information collector 51*a*, is preserved in the voice information preserver 52*b*. The voice information 62, which is collected by the X-ray-image-and-voice-information collector 51*a*, is preserved together with the time information, in the voice information preserver 52*b*. For example, the voice information preserver 52*b* preserves the voice information 62, which is collected by the X-ray-image-and-voice-information collector 51*a*, associated with elapsed time periods from the timing of the start of X-ray irradiation.

A timing identifier 51*d* for identifying a timing in which the speech of the patient is different from the examination sentence based on the voice information 62 preserved in the voice information preserver 52*b*. The speech of the patient is different from the examination sentence refers to that a sound that is produced by the patient in the speech is different from a sound that should be produced in the examination sentence. The normal information preserver 52*c* preserves normal information corresponding to the examination sentence. Specifically, the normal information preserver 52*c* preserves normal text information 63 representing the examination sentence as the normal information. The normal information preserver 52*c* is configured to be able to change the normal text information 63 as the normal information in accordance with the examination sentence. For example, a user changes the normal text information 63 as the normal information by using an operating part, such as an operating panel, included in the X-ray imaging apparatus 100.

The timing identifier 51*d* identifies the timing based on the normal information and the voice information 62. Specifically, the voice-to-text converter 51*b* converts the voice information 62 preserved in the voice information preserver 52*b* into text information by using predetermined speech conversion processing to produce converted text information 64. The voice-and-text comparator 51*c* compares the normal text information 63 with the converted text information 64. If the sound that is produced by the patient is different from the sound that should be produced in the examination sentence, the converted text information 64 includes a part in which a character is different from the normal text information 63 (different part). For this reason, the voice-and-text comparator 51*c* compares the normal text information 63 with the converted text information 64 to extract the different part.

The timing identifier 51*d* identifies the timing based on results of comparison between the normal text information 63 and the converted text information 64. Specifically, the timing identifier 51*d* extracts the timing (time information) in the voice information 62 corresponding to the different part, and identifies the timing extracted as the timing in which the speech of the patient is different from the examination sentence. If the voice-and-text comparator 51*c* extracts a plurality of different parts, the timing identifier 51*d* identifies timings corresponding to the plurality of different parts.

The X-ray image identifier 51*e* identifies a corresponding X-ray image 65 that corresponds to the timing that is identified by the timing identifier 51*d* in the plurality of X-ray images 61 preserved in the X-ray image preserver 52*a*. Specifically, the X-ray image identifier 51*e* identifies the X-ray image 61 that is collected at the same timing as the timing that is identified by the timing identifier 51*d* as the corresponding X-ray image 65. In a case in which one X-ray image 61 (an image of one frame) is identified as the X-ray image that is collected at the same timing as the timing that is identified by the timing identifier 51*d*, the X-ray image identifier 51*e* identifies the one X-ray image 61 as the corresponding X-ray image 65. Also, in a case in which two or more X-ray images 61 (images of two or more frames) are identified as the X-ray images that are collected at the same timing as the timing that is identified by the timing identifier 51*d*, the X-ray image identifier 51*e* identifies the two or more X-ray images 61 as the corresponding X-ray images 65. Also, in a case in which the timing identifier 51*d* identifies a plurality of timings, the X-ray image identifier 51*e* identifies the corresponding X-ray image 65 that corresponds to each of the plurality of timings.

The display controller 51*f* directs the display 30 to display the corresponding X-ray images 65 identified by the X-ray image identifier 51*e*. In this displaying, as shown in FIG. 3, the display controller **51*f* directs the display 30 to display parts of text information 66 on the examination sentences that correspond to the corresponding X-ray images 65 in addition to the corresponding X-ray images 65. In the exemplary displaying shown in FIG. 3, characters of normal examination sentences are displayed as the parts of text information 66. Characters of the converted text information 64 may be displayed as the text information 66. Also, the display controller 51*f* directs the display 30 to highlight a part of the examination sentence that is different from the speech of the patient in the part of the text information 66 on the examination sentence that corresponds to the corresponding X-ray image 65. In the exemplary displaying shown in FIG. 3**, parts of the speech of the patient that are different from the examination sentences are highlighted by underline and boldface. The parts of the speech of the patient that are different from the examination sentences may be highlighted by italics, enclosures or marks.

In a case in which one image is identified as the corresponding X-ray image 65, the display controller **51*f* directs the display 30 to display the one image identified as the corresponding X-ray image 65. In a case in which two or more images are identified as the corresponding X-ray images 65, the display controller 51*f* directs the display 30 to display one representative image that is a representative of the two or more images, which are identified as the corresponding X-ray image 65. Also, for example, the display controller 51*f* directs the display 30 to display all of the two or more images, which are identified as the corresponding X-ray images 65, side by side. Also, for example, the display controller 51*f* directs the display 30 to display the two or more images, which are identified as the corresponding X-ray images 65**, in a form of video to be reproduced in response to an operation input by the user.

Control Processing Relating to Patient's Speech Examination

Control processing of the X-ray imaging apparatus 100 relating to the examination of the speech of the patient according to this embodiment is now described with reference to a flowchart of FIG. 4. Here, processes in the flowchart are executed by the processing part 50.

Figure 4:
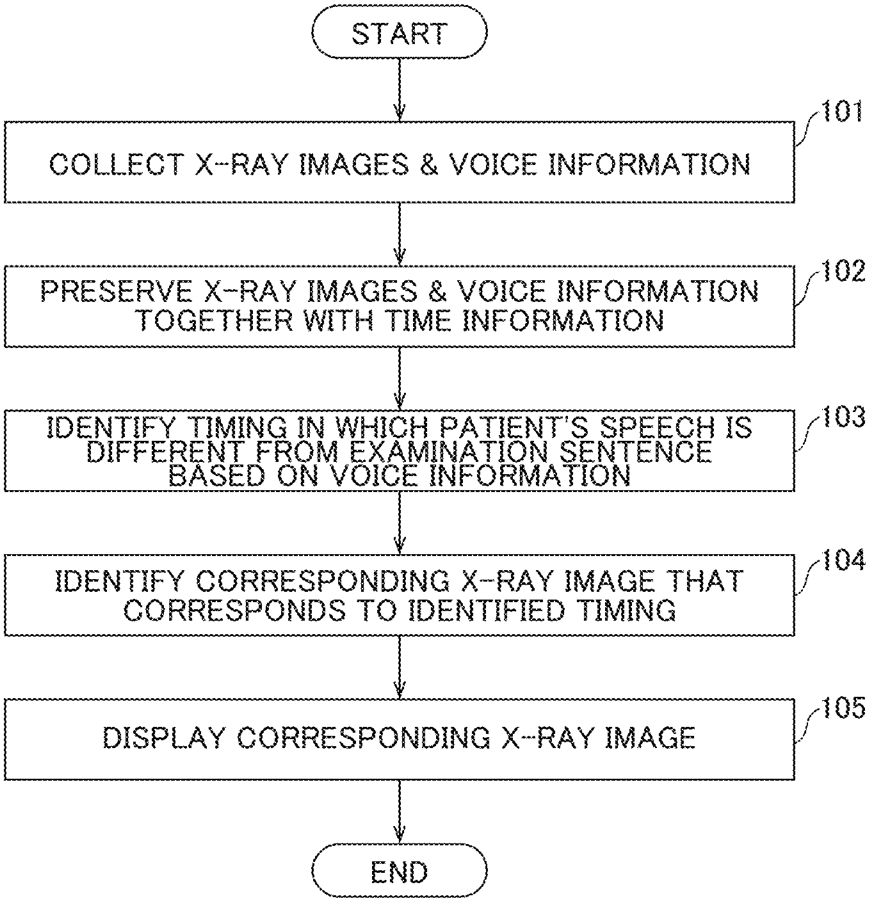
FIG. 4 is a flowchart illustrating control processing relating to the examination of the speech of the patient according to the one embodiment.

As shown in FIG. 4, in step 101, a plurality of X-ray images 61 are collected based on the detection results of the X-rays with which the patient is irradiated in a time width in which the patient produces the speech of the examination sentence, and the voice information 62 on the patient's voice input from the microphone 40 in a time width that at least partially overlaps the time width of the collection of the plurality of X-ray images 61 is collected. Subsequently, in step 102, both the plurality of X-ray images 61 and the voice information 62 collected are preserved together with time information.

Subsequently, in step 103, a timing in which speech of the patient is different from the examination sentence is identified based on the voice information 62 preserved. Subsequently, in step 104, a corresponding X-ray image 65 that corresponds to the timing that is identified in step 104 is identified in the plurality of X-ray images 61 preserved. Subsequently, in step 105, the corresponding X-ray image 65 is displayed on the display 30. After that, the control processing ends.

Advantages of the Embodiment

In this embodiment, the following advantages are obtained.

In this embodiment, as discussed above, a plurality of X-ray images 61 are collected based on detection results of the X-rays with which a patient is irradiated in a time width in which the patient produces speech of an examination sentence, and voice information 62 on the patient's voice input from a voice information 62 input part in a time width that at least partially overlaps the time width of the collection of the plurality of X-ray images; the plurality of X-ray images 61 collected are preserved together with time information; the voice information 62 collected is preserved together with time information; a timing in which speech of the patient is different from the examination sentence is identified based on the voice information 62 preserved; a corresponding X-ray image 65 that corresponds to the timing is identified from the plurality of X-ray images 61 preserved; and the corresponding X-ray image 65 is displayed on a display 30. According to this configuration, it is possible to automatically identify and display the corresponding X-ray image 65, which is the X-ray image 61 to be necessarily confirmed, in examination of speech of the patient. Consequently, radiologists are not required to find the X-ray image 61 to be necessarily confirmed from a large number of X-ray images 61 by themselves. As a result, it is possible to reduce burdens on the radiologists in examination of speech of patients.

Also, in this embodiment, as described above, a normal information preserver **52*c* for preserving normal information corresponding to the examination sentence is further provided; and the timing identifier 51*d* identifies the timing based on the normal information and the voice information 62. Accordingly, the timing in which speech of the patient is different from the examination sentence can be easily and accurately identified by using the normal information as compared with a case in which only the voice information 62** is used.

Also, in this embodiment, as described above, the normal information is normal text information 63 representing the examination sentence; a voice-to-text converter **51*b* for converting the voice information 62 preserved in the voice information preserver 52*b* into text information and producing converted text information 64, and a voice-and-text comparator 51*c* for comparing the normal text information 63 with the converted text information 64 are further provided; and the timing identifier 51*d* identifies the timing based on results of comparison between the normal text information 63 and the converted text information 64. Accordingly, since both types of the text information (the normal text information 63 and the converted text information 64) can be compared with each other, it is possible to easily and accurately obtain the results of comparison as compared with a case in which both types of the voice information are compared with each other without converting the voice information into the text information. Consequently, it is possible to easily and accurately identify the timing in which the speech of the patient is different from the examination sentence. Also, since text information (normal text information 63) is preserved as the normal information in the normal information preserver 52*c*, a data amount of the normal information can be reduced as compared with a case in which the voice information 62 is preserved as the normal information in the normal information preserver 52*c*. Consequently, it is possible to save a storage area in the normal information preserver 52*c*** that is used to store the normal information.

In this embodiment, as described above, the normal information preserver **52*c*** is configured to be able to change the normal information in accordance with the examination sentence. Accordingly, even in a case in which the examination sentence varies depending on facilities (e.g., hospitals) for conducting examination of speech of patients, the normal information can be appropriately changed in accordance with the examination sentence, which varies depending on the facilities. Also, in a case in which the examination sentence is changed in a facility, the normal information can be appropriately changed in accordance with the examination sentence changed. Consequently, the timing can be properly identified by using normal information.

Also, in this embodiment, as described above, the display controller 51*f* directs the display 30 to display parts of text information 66 on the examination sentences that correspond to the corresponding X-ray images 65 in addition to the corresponding X-ray images 65. Accordingly, radiologists do not necessarily find not only the corresponding X-ray image 65 but also the parts of text information 66 on the examination sentences that correspond to the corresponding X-ray images 65 by themselves. Consequently, it is possible to further reduce burdens on the radiologists in examination of speech of patients.

Also, in this embodiment, as described above, the display controller 51*f* directs the display 30 to highlight a part of the examination sentence that is different from the speech of the patient in each part of the text information 66 on the examination sentence that corresponds to the corresponding X-ray image 65. Accordingly, the radiologists can easily and accurately confirm the part of the examination sentence that is different from the speech of the patient. Consequently, it is possible to more easily reduce burdens on the radiologists.

Also, in this embodiment, as described above, the X-ray-image-and-voice-information collector 51*a* collects the plurality of X-ray images 61 and the voice information 62 on the patient's voice in synchronization with each other. Accordingly, since the plurality of X-ray images 61 and the voice information 62 on the patient's voice are collected in synchronization with each other, it is possible to easily and accurately identify the corresponding X-ray image 65.

MODIFIED EMBODIMENTS

Note that the embodiment disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

While the example in which the X-ray imaging apparatus is used for examination of patients' articulation impairment has been shown in the aforementioned embodiment, the present invention is not limited to this. In the present invention, the X-ray imaging apparatus may be used for examination other than examination of patients' articulation impairment as long as speech of patients is examined.

Also, while the example in which the X-ray imaging apparatus includes the microphone has been shown in the aforementioned embodiment, the present invention is not limited to this. In the present invention, the X-ray imaging apparatus may include no microphone. Voice information on patients' voice may be input to the X-ray imaging apparatus from an external microphone.

Also, while the example in which the X-ray imaging apparatus includes the display has been shown in the aforementioned embodiment, the present invention is not limited to this. In the present invention, the X-ray imaging apparatus may include no display. Image information may be output from the X-ray imaging apparatus to an external display so that the corresponding X-ray image and the like may be displayed on the external display.

Also, while the example in which the normal information is the normal text information has been shown in the aforementioned embodiment, the present invention is not limited to this. In the present invention, the normal information may be normal voice information representing the examination sentence. In this configuration, the X-ray imaging apparatus may include a voice information comparator for comparing the normal voice information with the voice information preserved in the voice information preserver, and the timing identifier may identify a timing in which the speech of the patient is different from the examination sentence based on results of comparison between the normal voice information and the voice information preserved in the voice information preserver.

Also, while the example in which a timing in which speech of the patient is different from the examination sentence is identified based on the normal information and the voice information has been shown in the aforementioned embodiment, the present invention is not limited to this. In the present invention, the timing in which speech of the patient is different from the examination sentence may be identified from the voice information by using AI techniques, such as machine learning models. For example, the timing in which speech of the patient is different from the examination sentence may be identified by using a machine learning model that is produced to output the timing in which the speech of the patient is different from the examination sentence when voice information is input by machine learning. Also, for example, the timing in which speech of the patient is different from the examination sentence may be identified by using a machine learning model that is produced to output the timing in which the speech of the patient is different from the examination sentence when converted text information into which the voice information is converted is input by machine learning.

Also, while the example in which the display controller directs the display to display a part of text information on the examination sentence that corresponds to the corresponding X-ray image in addition to the corresponding X-ray image has been shown in the aforementioned embodiment, the present invention is not limited to this. In the present invention, the part of the text information on the examination sentence that corresponds to the corresponding X-ray image may not be displayed on the display as long as the corresponding X-ray image is displayed on the display. Also, in a case in which the display displays the part of the text information on the examination sentence that corresponds to the corresponding X-ray image, the display may not highlight the part of the examination sentence that is different from the speech of the patient in the part of the text information on the examination sentence that corresponds to the corresponding X-ray image.

Also, while the example in which the plurality of X-ray images and the voice information on the patient's voice are collected in synchronization with each other has been shown in the aforementioned embodiment, the present invention is not limited to this. In the present invention, the plurality of X-ray images and the voice information on the patient's voice may not be collected in synchronization with each other. In this configuration, the X-ray image that has time information closest to the timing in which the speech of the patient is different from the examination sentence identified by the timing identifier may be identified as the corresponding X-ray image.

Also, in the aforementioned embodiment, voice information that corresponds to the corresponding X-ray image displayed on the display may be reproduced when a user inputs a predetermined operation during the corresponding X-ray image is displayed on the display. In other words, when the user inputs the predetermined operation, a part of the speech of the patient that is different from the examination sentence in the voice information may be reproduced.

MODES

It is understood by those skilled in the art that the exemplary embodiments described above are specific examples of the following aspects.

Mode Item 1

An X-ray imaging apparatus according to mode item 1 includes an X-ray irradiator for irradiating a patient with X-rays; an X-ray detector for detecting the X-rays with which the patient is irradiated by the X-ray irradiator; an X-ray-image-and-voice-information collector for collecting a plurality of X-ray images based on detection results of the X-rays with which the patient is irradiated in a time width in which the patient produces speech of an examination sentence, and for collecting voice information on the patient's voice input from a voice information input part in a time width that at least partially overlaps the time width of the collection of the plurality of X-ray images; an X-ray image preserver for preserving the plurality of X-ray images, which are collected by the X-ray-image-and-voice-information collector, together with time information; a voice information preserver for preserving the voice information, which is collected by the X-ray-image-and-voice-information collector, together with time information; a timing identifier for identifying a timing in which the speech of the patient is different from the examination sentence based on the voice information preserved in the voice information preserver; an X-ray image identifier for identifying a corresponding X-ray image that corresponds to the timing in the plurality of X-ray images preserved in the X-ray image preserver; and a display controller for directing a display to display the corresponding X-ray image.

Mode Item 2

In the X-ray imaging apparatus according to mode item 1, a normal information preserver for preserving normal information corresponding to the examination sentence is further provided; and the timing identifier identifies the timing based on the normal information and the voice information.

Mode Item 3

In the X-ray imaging apparatus according to mode item 2, the normal information is normal text information representing the examination sentence; the X-ray imaging apparatus further includes a voice-to-text converter for converting the voice information preserved in the voice information preserver into text information and producing converted text information, and a voice-and-text comparator for comparing the normal text information with the converted text information; and the timing identifier identifies the timing based on a result of comparison between the normal text information and the converted text information.

Mode Item 4

In the X-ray imaging apparatus according to mode item 2 or 3, the normal information preserver is configured to be able to change the normal information in accordance with the examination sentence.

Mode Item 5

In the X-ray imaging apparatus according to any of mode items 1 to 4, the display controller directs the display to display a part of text information on the examination sentence that corresponds to the corresponding X-ray image in addition to the corresponding X-ray image.

Mode Item 6

In the X-ray imaging apparatus according to mode item 5, the display controller directs the display to highlight a part of the examination sentence that is different from the speech of the patient in the part of the text information on the examination sentence that corresponds to the corresponding X-ray image.

Mode Item 7

In the X-ray imaging apparatus according to any of mode items 1 to 6, the X-ray-image-and-voice-information collector collects the plurality of X-ray images and the voice information on the patient's voice in synchronization with each other.

Mode Item 8

An processing apparatus according to mode item 8 includes an X-ray-image-and-voice-information collector for collecting a plurality of X-ray images based on detection results of X-rays with which a patient is irradiated in a time width in which the patient produces speech of an examination sentence, and for collecting voice information on the patient's voice input from a voice information input part in a time width that at least partially overlaps the time width of the collection of the plurality of X-ray images; an X-ray image preserver for preserving the plurality of X-ray images, which are collected by the X-ray-image-and-voice-information collector, together with time information; a voice information preserver for preserving the voice information, which is collected by the X-ray-image-and-voice-information collector, together with time information; a timing identifier for identifying a timing in which the speech of the patient is different from the examination sentence based on the voice information preserved in the voice information preserver; an X-ray image identifier for identifying a corresponding X-ray image that corresponds to the timing in the plurality of X-ray images preserved in the X-ray image preserver; and a display controller for directing a display to display the corresponding X-ray image.

Mode Item 9

An examination method according to mode item 9 includes a step of collecting a plurality of X-ray images based on detection results of X-rays with which a patient is irradiated in a time width in which the patient produces speech of an examination sentence, and for collecting voice information on the patient's voice input from a voice information input part in a time width that at least partially overlaps the time width of the collection of the plurality of X-ray images; a step of preserving the plurality of X-ray images collected together with time information; a step of preserving the voice information collected together with time information; a step of identifying a timing in which speech of the patient is different from the examination sentence based on the voice information preserved; a step of identifying a corresponding X-ray image that corresponds to the timing in the plurality of X-ray images preserved; and a step of displaying the corresponding X-ray image on a display.

What is claimed is:

1. An X-ray imaging apparatus comprising:
- an X-ray irradiator for irradiating a patient with X-rays;
- an X-ray detector for detecting the X-rays with which the patient is irradiated by the X-ray irradiator;
- an X-ray-image-and-voice-information collector for collecting a plurality of X-ray images based on detection results of the X-rays with which the patient is irradiated in a time width in which the patient produces speech of an examination sentence, and for collecting voice information on the patient's voice input from a voice information input part in a time width that at least partially overlaps the time width of the collection of the plurality of X-ray images;
- an X-ray image preserver for preserving the plurality of X-ray images, which are collected by the X-ray-image-and-voice-information collector, together with time information;
- a voice information preserver for preserving the voice information, which is collected by the X-ray-image-and-voice-information collector, together with time information;
- a timing identifier for identifying a timing in which the speech of the patient is different from the examination sentence based on the voice information preserved in the voice information preserver;
- an X-ray image identifier for identifying a corresponding X-ray image that corresponds to the timing in the plurality of X-ray images preserved in the X-ray image preserver; and
- a display controller for directing a display to display the corresponding X-ray image.

2. The X-ray imaging apparatus according to claim 1 further comprising a normal information preserver for preserving normal information corresponding to the examination sentence, wherein
- the timing identifier identifies the timing based on the normal information and the voice information.

3. The X-ray imaging apparatus according to claim 2, wherein
- the normal information is normal text information representing the examination sentence;
- the X-ray imaging apparatus further comprises a voice-to-text converter for converting the voice information preserved in the voice information preserver into text information and producing converted text information, and
- a voice-and-text comparator for comparing the normal text information with the converted text information; and
- the timing identifier identifies the timing based on a result of comparison between the normal text information and the converted text information.

4. The X-ray imaging apparatus according to claim 2, wherein the normal information preserver is configured to be able to change the normal information in accordance with the examination sentence.

5. The X-ray imaging apparatus according to claim 1, wherein the display controller directs the display to display a part of text information on the examination sentence that corresponds to the corresponding X-ray image in addition to the corresponding X-ray image.

6. The X-ray imaging apparatus according to claim 5, wherein the display controller directs the display to highlight a part of the examination sentence that is different from the speech of the patient in the part of the text information on the examination sentence that corresponds to the corresponding X-ray image.

7. The X-ray imaging apparatus according to claim 1, wherein the X-ray-image-and-voice-information collector collects the plurality of X-ray images and the voice information on the patient's voice in synchronization with each other.

8. A processing apparatus comprising:
- an X-ray-image-and-voice-information collector for collecting a plurality of X-ray images based on detection results of X-rays with which a patient is irradiated in a time width in which the patient produces speech of an examination sentence, and for collecting voice information on the patient's voice input from a voice information input part in a time width that at least partially overlaps the time width of the collection of the plurality of X-ray images;
- an X-ray image preserver for preserving the plurality of X-ray images, which are collected by the X-ray-image-and-voice-information collector, together with time information;
- a voice information preserver for preserving the voice information, which is collected by the X-ray-image-and-voice-information collector, together with time information;
- a timing identifier for identifying a timing in which the speech of the patient is different from the examination sentence based on the voice information preserved in the voice information preserver;
- an X-ray image identifier for identifying a corresponding X-ray image that corresponds to the timing in the plurality of X-ray images preserved in the X-ray image preserver; and
- a display controller for directing a display to display the corresponding X-ray image.

9. An examination method comprising:
- a step of collecting a plurality of X-ray images based on detection results of X-rays with which a patient is irradiated in a time width in which the patient produces speech of an examination sentence, and for collecting voice information on the patient's voice input from a voice information input part in a time width that at least partially overlaps the time width of the collection of the plurality of X-ray images;
- a step of preserving the plurality of X-ray images collected together with time information;
- a step of preserving the voice information collected together with time information;
- a step of identifying a timing in which speech of the patient is different from the examination sentence based on the voice information preserved;
- a step of identifying a corresponding X-ray image that corresponds to the timing in the plurality of X-ray images preserved; and a step of displaying the corresponding X-ray image on a display.

* * * * *